US006297058B1

(12) United States Patent
Reents, Jr.

(10) Patent No.: US 6,297,058 B1
(45) Date of Patent: Oct. 2, 2001

(54) PROCESS FOR DETERMINING IMPURITIES IN REFRACTORY MATERIALS

(75) Inventor: William David Reents, Jr., Middlesex, NJ (US)

(73) Assignee: Agere Systems Optoelectronics Guardian Corp., Orlando, FL (US)

( * ) Notice: Subject to any disclaimer, the term of this patent is extended or adjusted under 35 U.S.C. 154(b) by 0 days.

(21) Appl. No.: 09/231,025

(22) Filed: Jan. 14, 1999

(51) Int. Cl.$^7$ ................................................... G01N 33/38
(52) U.S. Cl. ..................... 436/145; 430/133; 430/144; 430/155; 430/173; 430/181; 250/282
(58) Field of Search ................................. 250/281, 282; 436/145, 133, 144, 155, 173, 181

(56) References Cited

U.S. PATENT DOCUMENTS

| | | | |
|---|---|---|---|
| 4,560,816 | 12/1985 | Davis, Jr. | 585/266 |
| 4,849,175 | 7/1989 | Dupain et al. | 422/63 |
| 5,354,698 | 10/1994 | Cathey, Jr. | 437/20 |

FOREIGN PATENT DOCUMENTS

| | | | |
|---|---|---|---|
| 137016 | * 8/1979 | (DD) | . |
| 05126733 | 9/1993 | (JP) | . |
| 6-271321 | * 9/1994 | (JP) | . |
| 481554 | * 12/1975 | (SU) | . |

OTHER PUBLICATIONS

F. W. Giacobbe et al, Sprechsaal 1988, 121, 776–780, Sep. 1988.*
D. R. Wall et al, J. Am. Ceram. Soc. 1990, 73, 2944–2952, Oct. 1990.*
H. Y. Sohn et al. J. Am. Ceram. Soc. 1990, 73, 2953–2961, Oct. 1990.*
P. J. Jorgensen et al, Phys. Chem. Glasses 1969, 10, 23–27, Feb. 1969.*
L. J. Rigby Dyn. Mass Spectrom. 1972, 3, 237–242.*
H. Mairlot C. R.—Symp. Elaboration Verre 1974, 391–404.*
I. I. Cheremisin et al, Prib. Tekh. Eksp. 1974, 134–137, Apr. 1974.*
R. Moore J. Vac. Sci. Technol. 1979, 16, 748–751, Mar. 1979.*
F. Kramer Glastechn. Ber. 1980, 53, 177–188, Jul. 1980.*
A. Breth et al, Ber. Oesterr. Studienges Atomenerg. 1980, SAGE Ber. No. 4008, 12 pages.*
M. Suppra Wiss. Z.—Friedrich–Schiller–Univ. Jena, Math-.–Naturwiss. Reihe 1980, 29, 795–600.*
M. N. Kovalev et al, Fiz. Khim. Stekla 1981, 7, 729–731, Jun. 1981.
K. Heide J. Therm. Anal. 1989, 35, 305–318, Feb. 1989.
F. W. Kramer Glastech. Ber. 1992, 65, 93–98, Apr. 1992.
M. Ishikawa et al. Taikabutsu 1997, 49, 505–509, Sep. 1997.
G. Volksch et al., "Dissolved gases and minor component effects on glass crystallization" *Journal of Non–Crystalline Solids*, vol. 219, pp. 119–127 (1997).
S. Yasufuku, "Application of thermal analysis techniques to appraisal and quality control in Japan", *IEEE Electrical Insulation Magazine*, vol. 6, No. 1 pp. 23–33 (1991).

* cited by examiner

*Primary Examiner*—Arlen Soderquist
(74) *Attorney, Agent, or Firm*—Scott J. Rittman

(57) ABSTRACT

A small sample of a refractory material, e.g., about 0.1 g to about 10 g, is heated to at least 1000° C., generally under a pressure of less than about $10^{-5}$ Torr. Evolved hydrogen-containing gases and/or carbon-containing gases are monitored, e.g., by mass spectrometry, and, based on the amount of the evolved gases, the concentration of hydrogen and/or carbon in the sample is calculated. It is therefore possible to accurately determine the hydrogen and carbon concentration from a small sample of a material, by a process much less burdensome than conventional techniques.

8 Claims, 3 Drawing Sheets

PROCESS FOR DETERMINING IMPURITIES IN REFRACTORY MATERIALS

BACKGROUND OF THE INVENTION

1. Field of the Invention

The invention relates to fabrication of glass optical fiber, including fabrication of preforms for forming such fiber.

2. Discussion of the Related Art

As the use of glass optical fiber has increased, the demand for stronger, more durable fibers with improved optical properties has similarly grown. Loss mechanisms and structural faults in optical fiber, e.g., bubbles, typically result from imperfections and impurities existing in the glass preform from which the fiber is drawn, and much effort has gone into finding useful ways to detect, monitor, and reduce, remove, or eliminate these imperfections and impurities. Problems encountered in the detection and monitoring of impurities include the time required to obtain an accurate measurement, and the difficulty with which that measurement is made. For example, hydrogen impurities in silica articles for preform manufacture, e.g., tubes or core rods, are typically measured by forming a preform from the article or articles, drawing fiber from the preform, and measuring the OH absorption of light transmitted through the fiber. Thus, it is not possible to determine whether the material contains undesired amount of hydrogen without going through the entire fiber fabrication process. Similarly, carbon content of silica materials is generally measured by placing a relatively large sample, e.g., tens to hundreds of grams, into a furnace, baking and decomposing the silica, and measuring the evolved carbon dioxide at high temperatures (greater than 2000° C.). This method, however, takes a relatively long time, does not offer as high a precision as desired, demands a relatively large sample, and requires expensive apparatus.

Improved techniques for determining impurity content of glass preforms and/or the resultant fiber are therefore desired.

SUMMARY OF THE INVENTION

The invention provides a process for forming a refractory article, in which carbon and/or hydrogen impurities in a refractory material, particularly silica, are measured by an improved technique. According to the invention, a small sample of a refractory material, e.g., about 0.1 g to about 10 g, is heated to at least 1000° C. Evolved hydrogen-containing gases and/or carbon-containing gases are monitored, e.g., by mass spectrometry at a pressure of less than about $10^{-5}$ Torr, and, based on the amount of the evolved gases, the concentration of hydrogen and/or carbon in the sample is calculated. The process makes it possible to accurately determine the hydrogen and carbon concentration from a small sample of a material, by a process much less burdensome than conventional techniques. For example, it is possible to take a small sample from a preform, or from a tube or rod from which a preform will be formed, and determine from that sample if the carbon and hydrogen concentration are acceptable for optical fiber fabrication. This is in sharp contrast to the conventional need to draw fiber from a finished preform (for hydrogen determination) and/or obtain a large sample and particular equipment (for carbon determination).

In one embodiment, a small silica sample is cleaned, placed in a vacuum chamber, and heated to at least 1000° C., optionally at least 1400° C., and the evolved carbon-containing and hydrogen-containing gases are monitored by a mass spectrometer. Upon such heating, the evolved gases include hydrogen, carbon dioxide, and formaldehyde, from which the hydrogen and carbon concentration are calculated. Significantly, it has been found that after carbon evolution substantially ceases during the initial heating step, the addition of more hydrogen to the sample makes it possible, upon reheating, to evolve additional carbon-containing gases. This hydrogen addition/reheating technique therefore provides a more accurate determination of carbon concentration.

DETAILED DESCRIPTION OF THE INVENTION

Figure 1:
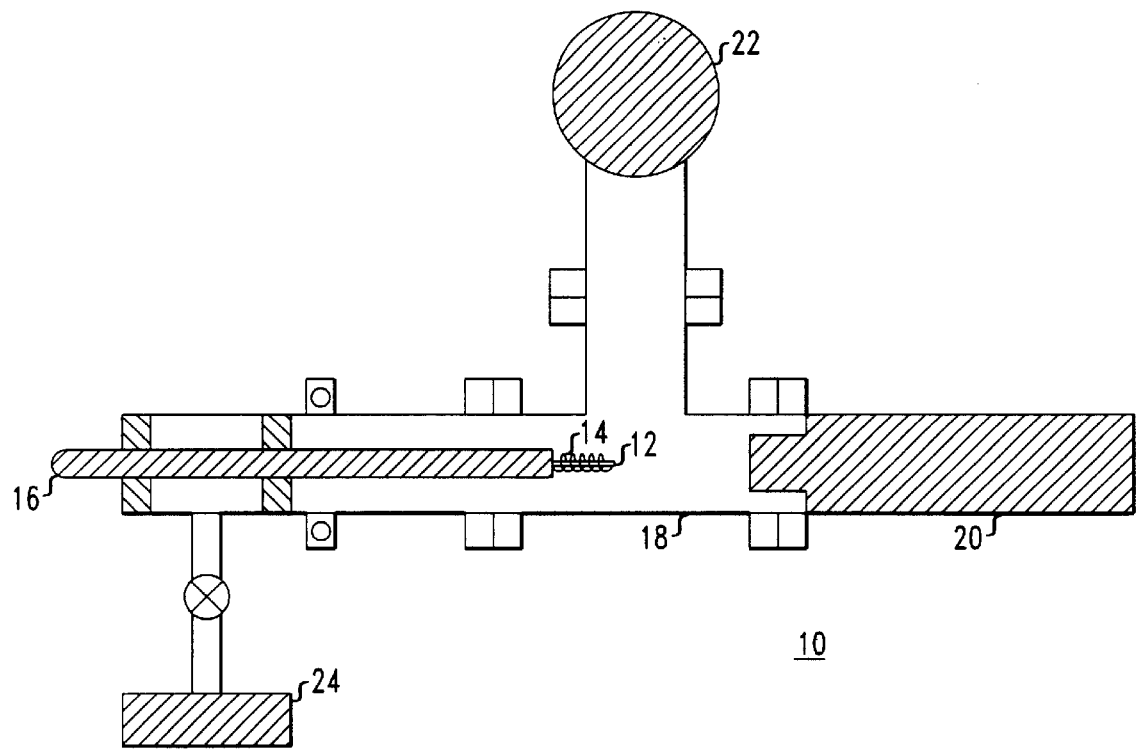
FIG. 1 illustrates an apparatus suitable for performing the process of the invention.

According to the invention, a sample of a refractory material, typically silica, is placed into a vacuum chamber. The sample is heated, and carbon-containing and/or hydrogen-containing gases evolved from the sample are monitored, such that the concentration of carbon and/or hydrogen in the sample is able to be calculated. It is also possible to observe other gases related to other impurities, e.g., HCl gas reflecting the presence of chlorine.

Typically, the sample is small, e.g., about 0.1 g to about 10 g, which makes the process easier and allows one to non-destructively test a body by taking such a small sampling of material. Thicker samples, for example, increase the difficulty in attaining an accurate measure. Specifically, gas will diffuse more slowly, i.e., over a longer time period, from a thick body, making signals weaker relative to noise and thereby affecting the detection limit. Increasing thickness also interferes with uniform heating. In determining an appropriate sample size, considerations include, but are not limited to, the rate of diffusion of the carbon- and hydrogen-containing gases (which should be adequate to obtain sufficient data sampling), the ability to raise the sample's temperature at a desired rate and to a desired temperature in a relatively uniform manner, and the detection limit of the apparatus. Typically, the parameters of the apparatus are able to be scaled to a particular sample size and rate of gas evolution.

The sample is generally cleaned, e.g., by soaking in concentrated HF for 30 to 60 seconds and then rinsing in deionized water for about 60 seconds. The sample is then heated, generally to at least 1000° C., optionally at least 1400° C. The final temperature reached should be selected to promote evolution of carbon- and hydrogen-containing gases, but not be so high as to thermally break down the sample material. The rate at which the temperature is reached is also relevant to the process, in that a fast temperature ramp-up tends to increase sensitivity due to higher outgassing in a shorter time period. Heating is performed by any suitable method. Typically, the sample is held and heated by a platinum coil, wire, ribbon, or grid which provides relatively uniform heating. Another option is pulsed laser heating, although such laser heating is point specific.

The evolved gases from the sample are monitored by any suitable detection technique, e.g., mass spectrometry, including quadrupole, ion-trap, or time-of-flight mass spectrometry. The pressure is typically less than about $10^{-5}$ Torr when using mass spectrometry, to allow accurate detection of the evolved gases, but is capable of varying depending on the particular detection device. Other possible techniques include monitoring pressure rise during evolution to get a non-specific impurity content, or evolving the impurities in an inert gas. The detection apparatus is arranged to monitor the evolved carbon-containing and hydrogen-containing gases. In the case of silica, such gases include hydrogen, carbon dioxide, and formaldehyde ($H_2CO$). Using standard techniques, the amount of evolved gas is converted into moles of gas, which in turn is used in combination with the original sample weight to determine concentration of carbon and/or hydrogen. For example, an integrated ion signal obtained by a mass spectrometer provides a total pressure-time product for the amount of evolved gas. Multiplying by the conductance of the vacuum system of the mass spectrometer produces a number capable of conversion to absolute moles of evolved gas. The mass of the gas is then calculated and related to the original sample weight to determine the concentration of hydrogen and carbon. Note that hydrogen and formaldehyde contribute to hydrogen content information, and carbon dioxide and formaldehyde contribute to carbon content information.

Control samples are easily prepared to determine an appropriate sample size and temperature regime for a given material and apparatus.

In addition to the steps above, which provide reliable measures of hydrogen and carbon concentration, it is possible to perform further steps to obtain even more accurate measurements of carbon content. Specifically, it has been found that in silica the amount of evolved carbon relates to the amount of hydrogen in a sample. For example, even if evolution of carbon-containing gases ceases during heating, a step of subsequently adding hydrogen to the sample, such as by immersing in a liquid or gaseous hydrogen-containing environment, e.g., concentrated HF for 30 to 60 seconds, will generally result in further evolution of carbon-containing species upon reheating of the sample. It is therefore possible to obtain an extremely accurate measure of carbon content by repeatedly heating the sample and monitoring the evolved gases, adding hydrogen, and reheating, until the hydrogen addition no longer promotes further carbon evolution. It is also possible to use this hydrogen-addition technique to rid a body of carbon, regardless of whether the evolved gases are monitored.

An apparatus 10 suitable for practicing the process is illustrated schematically in FIG. 1. A sample 12 is supported by a platinum coil 14 (which also heats the sample) attached to the end of a probe 16. The probe 16 inserts the sample 12 into a vacuum chamber 18, and the probe body provides a seal against the interior of the vacuum chamber. The sample 12 is located relatively close to a detection device 20. The vacuum chamber is evacuated using a high vacuum pump 22, e.g., a turbopump, backed with a mechanical pump 24. Upon heating of the sample 12, evolved gases are detected by the detection device 20, by whatever technique the particular device 20 utilizes. The amount of evolved gases are then converted, by standard techniques as discussed herein, into the carbon and hydrogen concentrations originally present in the sample.

The invention is useful in providing a radial profiling of carbon and/or hydrogen concentration in a body, e.g., a tubular or cylindrical body, due to the small sample size required. Specifically, as reflected in the Examples (and FIG. 2), it is possible to cut samples from particular radial positions of a body, e.g., exterior, bulk, and interior. The concentrations found in each particular sample provide the radial profile. It is also possible to obtain axial profiles by cutting samples along the length of a body.

The process of the invention is useful for forming a variety of refractory articles where it is desired to monitor the hydrogen and carbon content prior to the final fabrication steps. In particular, it is contemplated that optical fiber preforms, or the overcladding tubes, substrate tubes, or core rods from which preforms are made, will be tested for hydrogen and carbon impurities as early in their fabrication process as possible. It will therefore be possible to avoid the costs associated with drawing fiber or forming the preform, due to the ability to determine, at an early stage of manufacture, whether an article is unacceptable due to its carbon or hydrogen content.

The invention will be further clarified by the following examples, which are intended to be exemplary.

EXAMPLE 1

Figure 2:
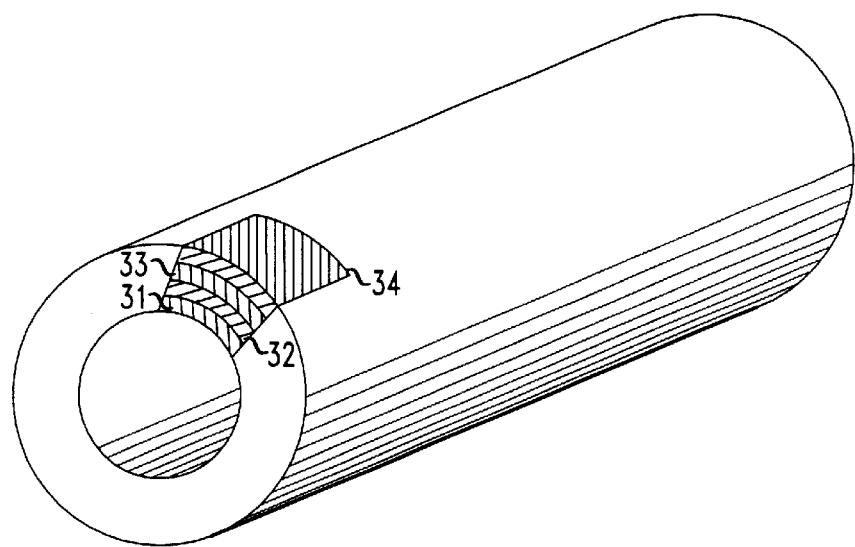
FIG. 2 illustrates the locations of samples taken from a silica tube according to Examples 1 and 2.

Four samples of silica glass, each about 1.6 mm×about 1.6 mm×40 mm, were cut from a silica glass tube 30, as shown in FIG. 2. Specifically, the four samples 31, 32, 33, 34, represent material from, respectively, the inner diameter of the tube, the bulk portion near the inner diameter, the bulk portion near the outer diameter, and the outer diameter. Each sample was tested as follows.

The sample was cleaned by soaking in 50% HF at room temperature for 60 seconds (which appears to introduce a negligible amount of H, if any), and then in deionized water for 30 seconds. Using an apparatus of the type illustrated in FIG. 1, the silica sample was then placed in the platinum coil of a CDS Pyroprobe heater (Model 122, with rate and time extender, obtained from Chemical Data Systems, Inc., Oxford, Pa., USA), and placed through a load-lock into a vacuum chamber. The sample was placed approximately 5 cm from the mass spectrometer ion source of a Hiden RC Residual Gas Analysis device (Hiden Analytical, Warrington, England, UK). The vacuum chamber was evacuated with a 300 l/s turbopump, backed by a 340 l/m mechanical pump.

Figure 3A:
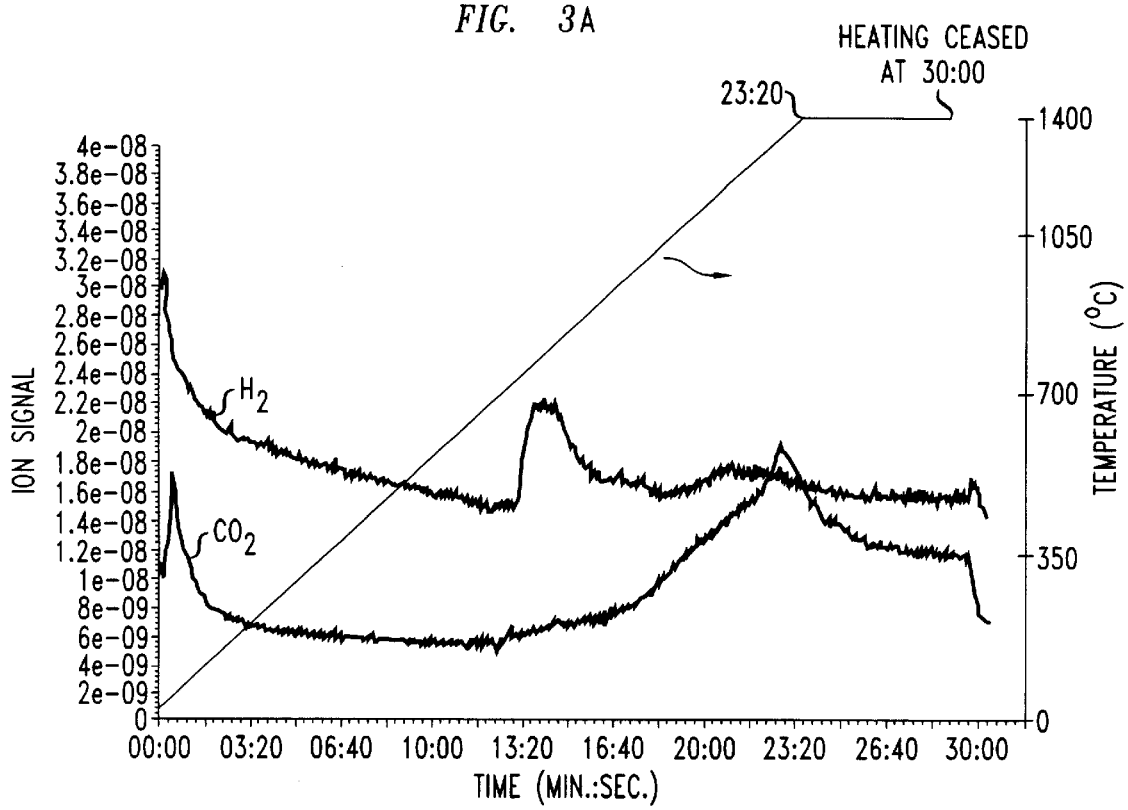
FIGS. 3A and 3B show the ion signals for hydrogen, carbon dioxide, and formaldehyde, along with the temperature profile, as a function of time, according to Example 1.
Figure 3B:
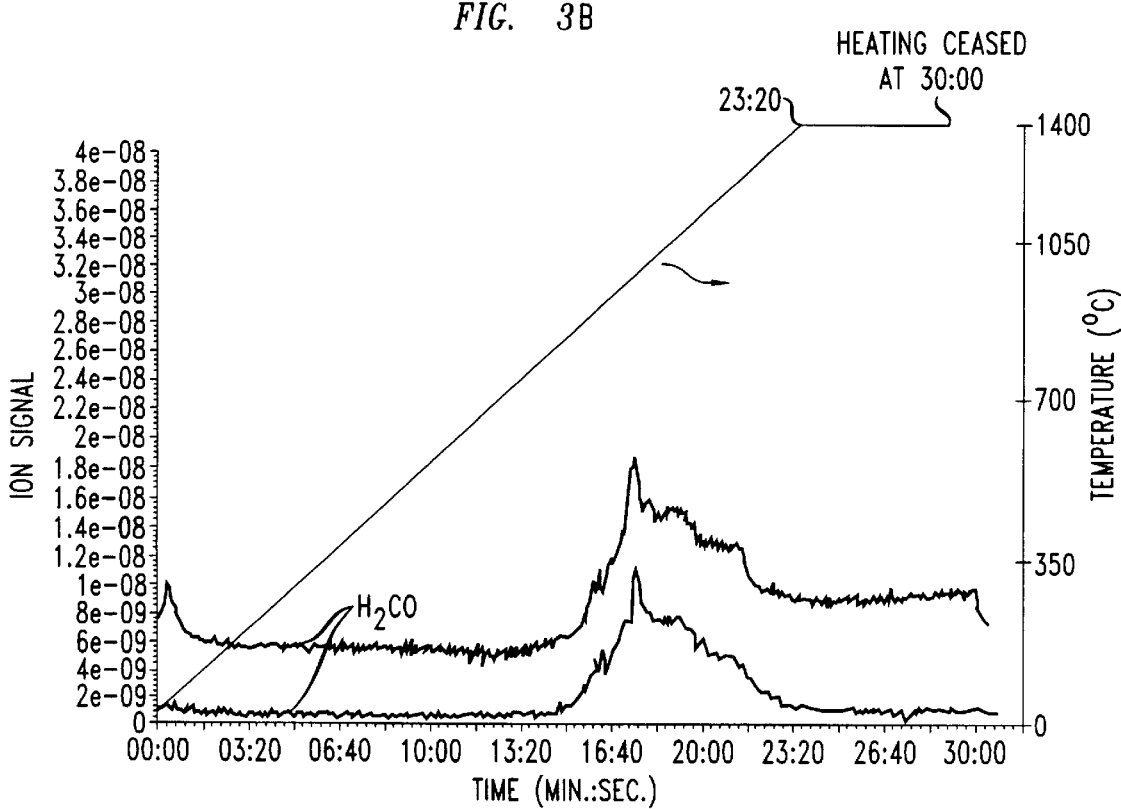

The silica sample was heated at a nominal rate of 62° C./minute to a final temperature of 1400° C., and held at this temperature (heat time plus time at 1400° C.) for 30 minutes. Mass spectrometer data acquisition began at the onset of heating. Data was acquired over 1 to 100 amu every 2.6 seconds. Single ion signals were extracted from the data to determine the extent of gas evolution for a particular impurity. FIGS. 3A and 3B show the ion signals for hydrogen, carbon dioxide, and formaldehyde, as noted on the Figures, for one of the samples, along with the temperature regime, as a function of time. (Ion signal is presented in units of Torr.)

EXAMPLE 2

Figure 4:
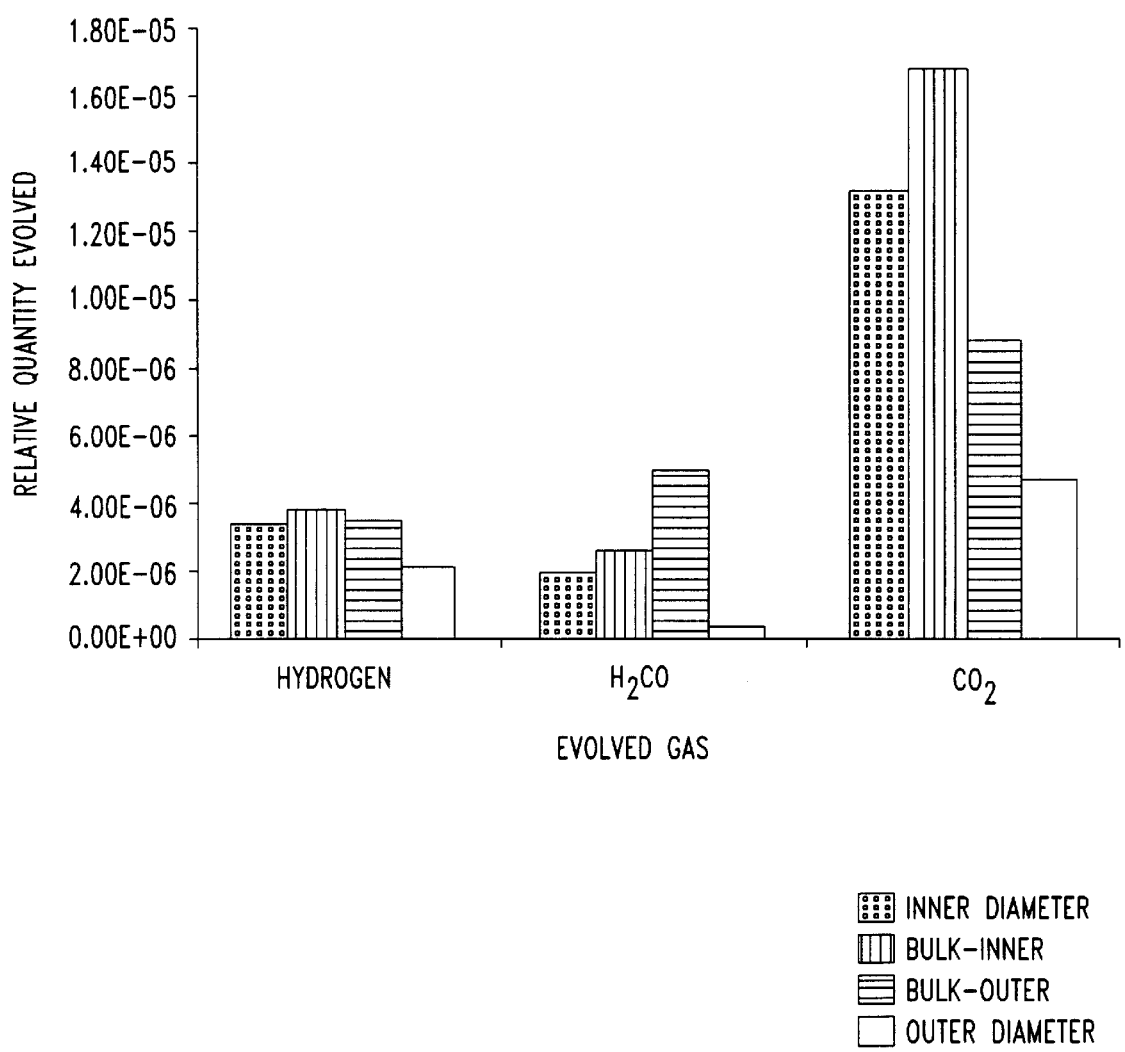
FIG. 4 shows the concentration of evolved hydrogen, formaldehyde, and carbon dioxide for several portions of a high-purity silica tube, according to Example 2.

The process of Example 1 was performed on a four samples cut in the same configuration as FIG. 2, but from a different silica tube. The same procedure as in Example 1 was performed to monitor evolved carbon- and hydrogen-containing gases. The concentration of evolved hydrogen, formaldehyde, and carbon dioxide are shown for the inner diameter, outer diameter, bulk—inner side, and bulk—outer side portions of the tube in FIG. 4, along with the temperature regime. Table 1 illustrates the concentration levels for carbon and hydrogen, as derived from the evolved gas data for the four samples. The values for carbon are lower limits because evolution of carbon dioxide and formaldehyde, as mentioned previously, appear to be limited by the availability of hydrogen in the silica.

TABLE 1

Hydrogen and Carbon Impurities as a Function of Location

| Sample Location | Hydrogen Concentration (parts per million, w/w) | Carbon Concentration (parts per million, w/w) |
|---|---|---|
| Inner diameter | 1.5 | 8 |
| Bulk - inner side | 1.8 | 8 |
| Bulk - outer side | 0.6 | 5 |
| Outer diameter | 0.4 | 2 |

Other embodiments of the invention will be apparent to those skilled in the art from consideration of the specification and practice of the invention disclosed herein.

What is claimed is:

1. A process for fabricating a refractory article, comprising the steps of:

(a) heating a silica sample to at least 1000° C.;

(b) monitoring at least one of evolved hydrogen-containing gases and evolved carbon-containing gases;

(c) cooling the sample and adding hydrogen to the cooled sample;

(d) subsequent to adding hydrogen, reheating the sample to at least 1000° C. and monitoring evolved carbon-containing gases;

(e) optionally repeating steps (c) and (d); and (f) based on the amount of the evolved gases, calculating the concentration of at least one of hydrogen and carbon in the sample.

2. The process of claim 1, wherein the sample has a weight of about 0.1 g to about 10 g.

3. The process of claim 1, wherein the sample is heated to at least 1400° C. during at least one of the heating step and the reheating step.

4. The process of claim 1, wherein the heating and reheating steps are performed at a pressure less than about $10^{-5}$ Torr, and wherein the monitoring is performed by mass spectrometry.

5. The process of claim 1, wherein the evolved gases comprise $H_2$, $CO_2$, and $H_2CO$.

6. The process of claim 1, wherein the sample is supported and heated by a platinum coil, wire, ribbon, or grid.

7. The process of claim 1, wherein a radial profile is obtained for at least one of carbon concentration and hydrogen concentration.

8. A process for fabricating a refractory article, comprising the steps of:

heating a silica body to at least 1000° C.;

cooling the body and adding hydrogen to the cooled body; and subsequent to adding hydrogen, reheating the body to at least 1000° C., wherein the added hydrogen promotes evolution of carbon-containing species from the body.

* * * * *